(12) United States Patent
Wright et al.

(10) Patent No.: US 9,797,697 B2
(45) Date of Patent: Oct. 24, 2017

(54) HYPER-VELOCITY IMPACT SENSOR

(71) Applicant: Raytheon Company, Waltham, MA (US)

(72) Inventors: Richard J. Wright, Tucson, AZ (US); James G. Sierchio, Tucson, AZ (US); William R. Owens, Tucson, AZ (US); Thomas M. Crawford, Marana, AZ (US); Myron E. Calkins, Jr., Tucson, AZ (US)

(73) Assignee: Raytheon Company, Waltham, MA (US)

( * ) Notice: Subject to any disclaimer, the term of this patent is extended or adjusted under 35 U.S.C. 154(b) by 141 days.

(21) Appl. No.: 14/730,746

(22) Filed: Jun. 4, 2015

(65) Prior Publication Data
US 2016/0356688 A1    Dec. 8, 2016

(51) Int. Cl.
| | |
|---|---|
| *F42B 12/36* | (2006.01) |
| *G01N 19/06* | (2006.01) |
| *G01P 15/06* | (2006.01) |
| *F42C 19/06* | (2006.01) |
| *G01N 9/00* | (2006.01) |
| *G01P 15/08* | (2006.01) |
| *G01B 5/06* | (2006.01) |
| *F42B 12/02* | (2006.01) |
| *G01B 11/06* | (2006.01) |
| *G01N 9/36* | (2006.01) |
| *F41J 5/06* | (2006.01) |

(52) U.S. Cl.
CPC .............. *F42B 12/365* (2013.01); *F41J 5/06* (2013.01); *F42B 12/02* (2013.01); *F42C 19/06* (2013.01); *G01B 5/06* (2013.01); *G01B 11/06* (2013.01); *G01N 9/36* (2013.01); *G01P 15/06* (2013.01); *G01P 15/0891* (2013.01); *G01N 9/00* (2013.01)

(58) Field of Classification Search
CPC ......... F42B 12/365; G01P 15/06; F41J 5/044; F41J 5/04
IPC ....................................................... G01P 15/06
See application file for complete search history.

(56) References Cited

U.S. PATENT DOCUMENTS

| | | | | |
|---|---|---|---|---|
| 3,447,077 A | * | 5/1969 | Wieland | .................. F41J 5/044 |
| | | | | 324/180 |
| 3,587,291 A | * | 6/1971 | Edward | .................. G01P 3/665 |
| | | | | 73/12.05 |
| 4,020,765 A | | 5/1977 | Glass et al. | |
| 4,411,198 A | | 10/1983 | Shrader et al. | |
| 5,546,358 A | * | 8/1996 | Thomson | ................ F41G 3/142 |
| | | | | 102/513 |

(Continued)

FOREIGN PATENT DOCUMENTS

JP          10300395 A     *  11/1998

OTHER PUBLICATIONS

Gorman et al., "Hypervelocity Impact (HVI)," NASA/CR-2007-214885/vol. 1, Digital Wave Corporation, Englewood, Colorado, Sep. 2007.

(Continued)

*Primary Examiner* — Daniel J Colilla
(74) *Attorney, Agent, or Firm* — Eric A. Gifford

(57) ABSTRACT

A hyper-velocity impact sensor is configured to probe a mass of material consumed upon impact with an object. The probe can extract density and thickness characteristics of the impacted object, which can be used to classify the object.

18 Claims, 7 Drawing Sheets

(56) References Cited

U.S. PATENT DOCUMENTS

| | | | |
|---|---|---|---|
| 7,189,959 B1 * | 3/2007 | Morison | G01L 5/0052 |
| | | | 250/227.14 |
| 8,307,694 B1 * | 11/2012 | Kiefer | G01S 5/06 |
| | | | 73/12.01 |
| 2010/0307363 A1 | 12/2010 | Chishinski | |
| 2012/0188078 A1 * | 7/2012 | Soles | G08B 13/126 |
| | | | 340/540 |

OTHER PUBLICATIONS

Jackson et al., "Fibre optic sensors for high speed hypervelocity impact studies and low velocity drop tests," 21st International Conference on Optical Fiber Sensors, Proc. of SPIE vol. 7753, 2011.
Jackson et al., "Fiber Optic Interrogation Systems for Hypervelocity and Low Velocity Impact Studies," Applied Optics Group, School of Physical Sciences, University of Kent, Canterbury, Kent,CT2 7NH, UK, Jun. 10, 2011.

* cited by examiner

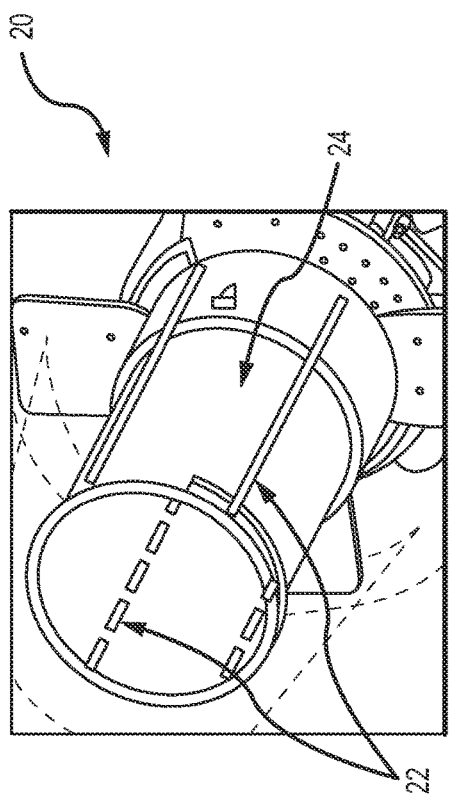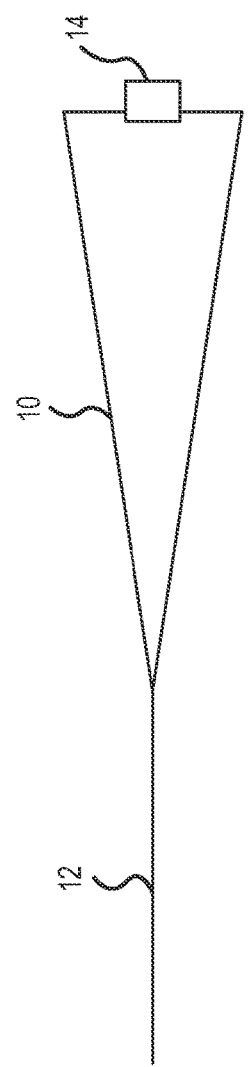

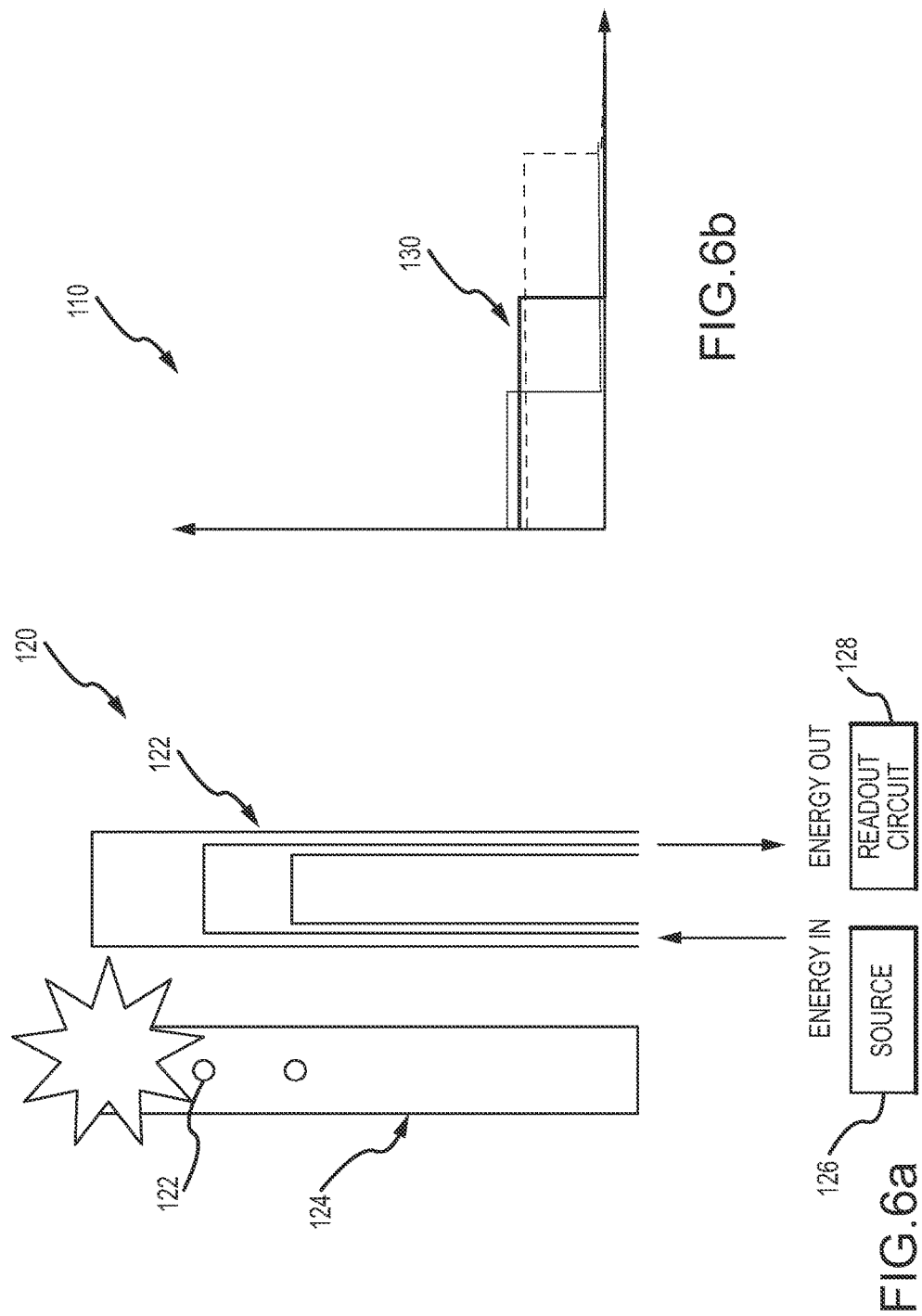

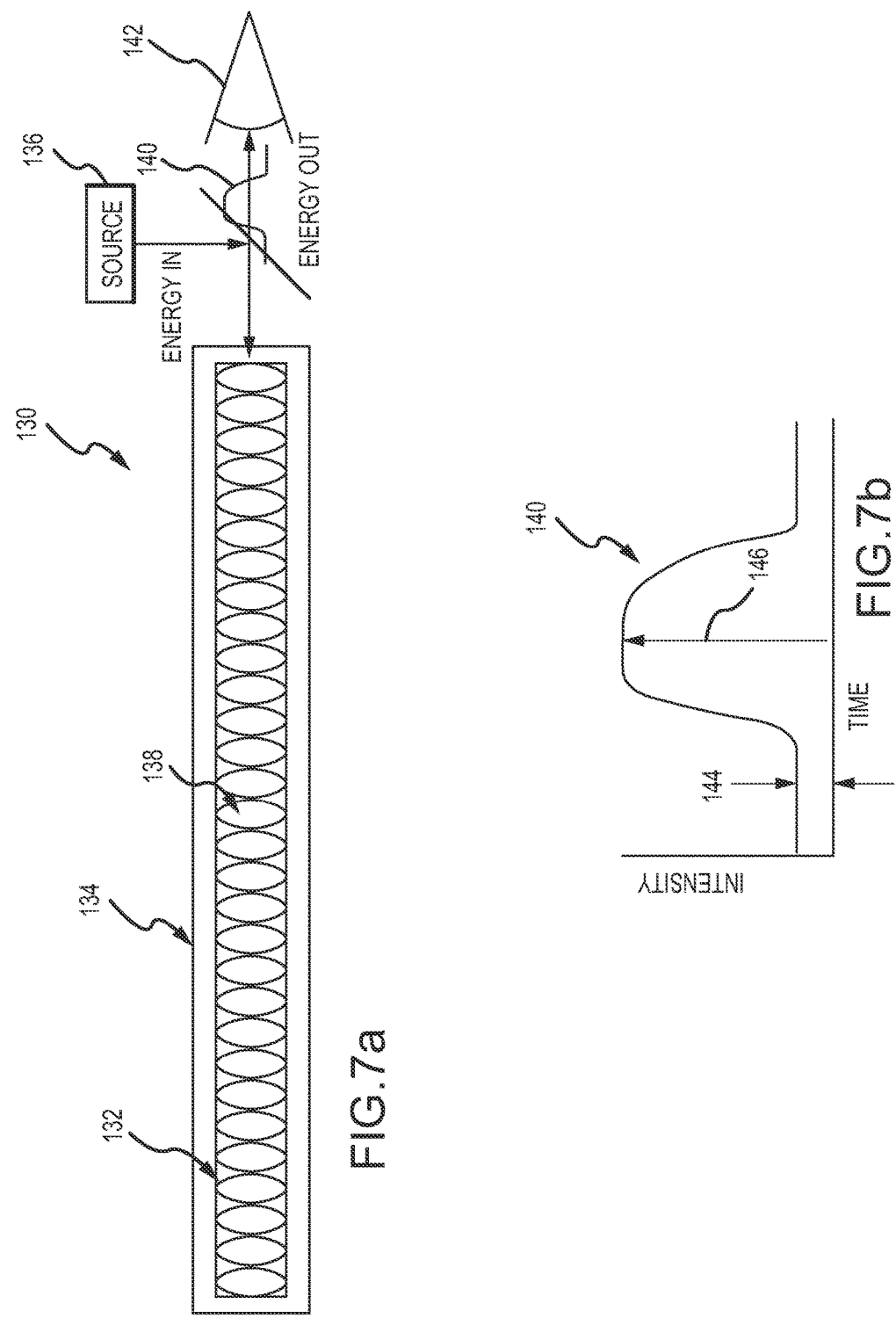

HYPER-VELOCITY IMPACT SENSOR

BACKGROUND OF THE INVENTION

Field of the Invention

This invention relates to impact sensors, and more particularly to a class of impact sensors for hyper-velocity impacts.

Description of the Related Art

Shock and impact sensors are devices that detect sudden movements, changes, or severe impacts at a predetermined level and indicate whether that level has been exceeded. Impact sensors are used in applications where it is desirable to know when an impact has occurred. In an ultra-high velocity impact, the relative velocities of the colliding objects can be about 5000 meters per second (m/s) or higher which is about the speed of sound in metal. The speed of sound through the metal construction materials of a projectile limits the propagation speed of the shock wave from an impact through the projectile. Under these conditions, the normal working assumptions of conventional technologies used in the art break down. An example of an application that uses this ultra-high velocity is an anti-projectile projectile. During the final flight stage of the projectile, high velocities are used to improve the accuracy and the efficacy of a successful engagement. In the case where it is desirable for a projectile to send a notification that it has had an impact, this event must be sensed, analyzed, and transmitted after the impact has occurred, but before the projectile is destroyed by the impact. The projectile's impact sensor needs to be able to detect that an impact has occurred before the sensor is destroyed. Related to this, the sensor must be able to trigger a notification message be sent, and the message sent before the transmitter is destroyed.

Conventional techniques use electrical sensors to detect an impact. Conventional techniques require that the shock from the impact arrive at the sensor and the sensor actuates before the sensor is destroyed. If the electrical sensor is positioned at the anticipated area of impact, the sensor will be destroyed on impact, hence unable to send an impact notification message. Another option for an electrical sensor is to position the sensor in an area of the projectile that is not near the area of impact and detect an indication of the impact. This method is not sufficient at ultra-high velocities because the velocity of the destructive shock wave through the projectile structure exceeds the speed of the sound in the materials of which the projectile is constructed, so the sensor is destroyed before being able to detect the impact.

Another option is to use a conductive circuit positioned at the anticipated area of impact and an electrical sensor positioned in a second area of the projectile, away from the anticipated area of impact. An electrical signal, such as a voltage, is supplied through the conductive circuit. The sensor monitors the conductive circuit for a change in the signal being supplied to the circuit. When the projectile impacts, the conductive circuit is destroyed before the sensor is destroyed. When the sensor measures a change in the signal being monitored, the change can be analyzed, and if this change indicates that the circuit has been destroyed, the sensor can trigger an impact notification message. This technique is known in the art and is used to measure impacts at velocities about 1000 m/s, which is much lower than speed of sound in the materials of which the projectile is constructed. At these velocities, the impact results in damage to the conductive circuit, for example breaking of the conductivity of the circuit. The corresponding change, in this example loss of signal in the circuit, is measured by the sensor, and an impact message can be sent before the sensor is destroyed.

This technique of using a conductive circuit is not sufficient to detect ultra-high velocity projectile impacts because of the type of destruction resulting from the impact. When there is an ultra-high velocity projectile impact, the construction material of the projectile transitions to an indefinite state. The unpredictable effects of an ultra-high velocity impact on electrical circuitry may be because of the possible formation of plasma, or other unpredictable physical phenomena, due to the velocity of the impact exceeding the speed of sound in the material. The operation of a conductive circuit under these conditions cannot be predicted reliably. The destruction of a conductive circuit at ultra-high velocities does not provide a reliable change in the signal. For example, the conductive circuit may short instead of breaking, or may have a non-repeatable response.

U.S. Patent Pub 2010/0307353 entitled "Ultra-high velocity projectile impact sensor" discloses an apparatus for detecting the impact of an ultra-high velocity projectile including: a projectile; at least one optical fiber attached to at least a first area of the projectile; a light source coupled to the at least one optical fiber supplying light into the at least one optical fiber; and a monitor coupled to the at least one optical fiber configured to monitor a property of the light in the at least one optical fiber and positioned in a second area of the projectile. An optical fiber provides a predictable response under the conditions of an ultra-high velocity projectile impact. When the optical fiber is intact, it propagates light and when the fiber is damaged, the light decreases. In the case where the optical fiber is broken or destroyed or even under some conditions of shock and vibration, the light cannot propagate or propagation is decreased through the optical circuit. Referring to FIGS. 2A-2D, schematic examples of some options for optical fiber layout, the optical fiber may be deployed in a variety of configurations. FIGS. 2A-2C are examples of laying out the cable on the substrate in several optional configurations. FIG. 2D is an example of deploying more than one optical fiber cable on a substrate. It is also possible to use more than one substrate.

When a projectile strikes a target, the impact will be at a first area of the projectile. Depending on the design of the projectile, this first area will begin to crush, collapse, fragment, explode, or similar. Given the ultra-high velocity of the impact, high energies are involved and the materials at the first area of the projectile begin to transition to an indefinite and/or unpredictable state. The optical fiber in the first area is possibly deformed, then destroyed, resulting in an interruption to the light propagating through the optical fiber. The shockwave from the impact begins to travel through the projectile from the first area of impact toward the second area farther away from the impact. The velocity of light in fiber is significantly faster than even ultra-high velocity impacts of a projectile with a target. This difference in velocities allows the monitor to detect a change in the light at the second area before the shockwave reaches the second area and damages or destroys the monitor.

SUMMARY OF THE INVENTION

The following is a summary of the invention in order to provide abasic understanding of some aspects of the invention. This summary is not intended to identify key or critical elements of the invention or to delineate the scope of the invention. Its sole purpose is to present some concepts of the invention in a simplified form as a prelude to the more detailed description and the defining claims that are presented later.

The present invention provides a hyper-velocity impact sensor that measures an amount of material consumed at impact to estimate the density and possibly thickness of the impacted object. This information can be used to classify the object.

In an embodiment, an impact sensor comprises a reference material configured such that varying and known amounts of the material are consumed during impact with different objects of known density and possibly thickness at closing velocities within a specified range. A probe along the length of the reference material is configured to generate an output indicative of the amount of the material consumed during impact. A circuit is configured to readout a probe output (or temporal sequence of probe outputs). A processor is configured to process the probe output(s) to estimate the density (and possibly thickness) of the impacted object to classify the object. The reference material and probe are configured to extend from an impact area aft to a rear area where the circuit may readout the probe output before it is consumed. The processor may be located with the circuit or remotely. Either the raw or processed outputs are transmitted to a remote location before the impact sensor is fully consumed.

In an embodiment, the impact and consumption of material produces a pulse of energy in the form of a flash and heat. The pulse height provides information about impact velocity and the density of the impacted object. The pulse width provides information about impact velocity and the thickness of the impacted object. The probe is configured to generate probe outputs indicative of the amount and rate of material consumed by the pulse of energy. The circuit reads out a time sequence of the probe outputs, which the processor processes to extract height and width of the pulse to estimate density and thickness of the impacted object. The processor may extract and use this information either implicitly (e.g. matched filters) or explicitly (calculate density and thickness) to classify the impacted object.

In an embodiment, the probe and readout circuit are configured to transmit the pulse along the length of the probe to the readout circuit. In one configuration, a fiber optic probe is optically coupled to an optical detector. The optical pulse travels inside the fiber optic probe to the optical detector. In another configuration, a 2-wire or coaxial cable provides an electrical probe that is coupled to a readout circuit. The plasma that forms the pulse of energy is conductive, and thus will produce an electrical pulse that travels along the 2-wire or coaxial cable to the readout circuit.

In an embodiment, the probe is a multi-element probe in which the elements change output state as differing amounts of the reference material, hence additional elements of the probe at differing depths, are consumed. The readout circuit reads out a temporal sequence of the output states. The multi-element probe may be optical or electrical. A source is required to provide an optical or electrical signal to the probe.

In an embodiment, the probe includes a source of energy (RF, optical, acoustic) and a cavity that are configured to create a standing wave pattern. As the probe is consumed by the pulse of energy, the standing waves collapse and the energy stored therein travels out of the end of the cavity forming a pulse that is coupled to a detector.

These and other features and advantages of the invention will be apparent to those skilled in the art from the following detailed description of preferred embodiments, taken together with the accompanying drawings, in which:

BRIEF DESCRIPTION OF THE DRAWINGS

FIGS. 1a and 1b are depictions of a projectile outfitted with an impact sensor;

FIGS. 6a and 6b are diagrams of a multi-element (electronic or fiber optic) impact sensor; and FIGS. 7a and 7b are diagrams of a standing-wave impact sensor.

DETAILED DESCRIPTION OF THE INVENTION

Figure 2:
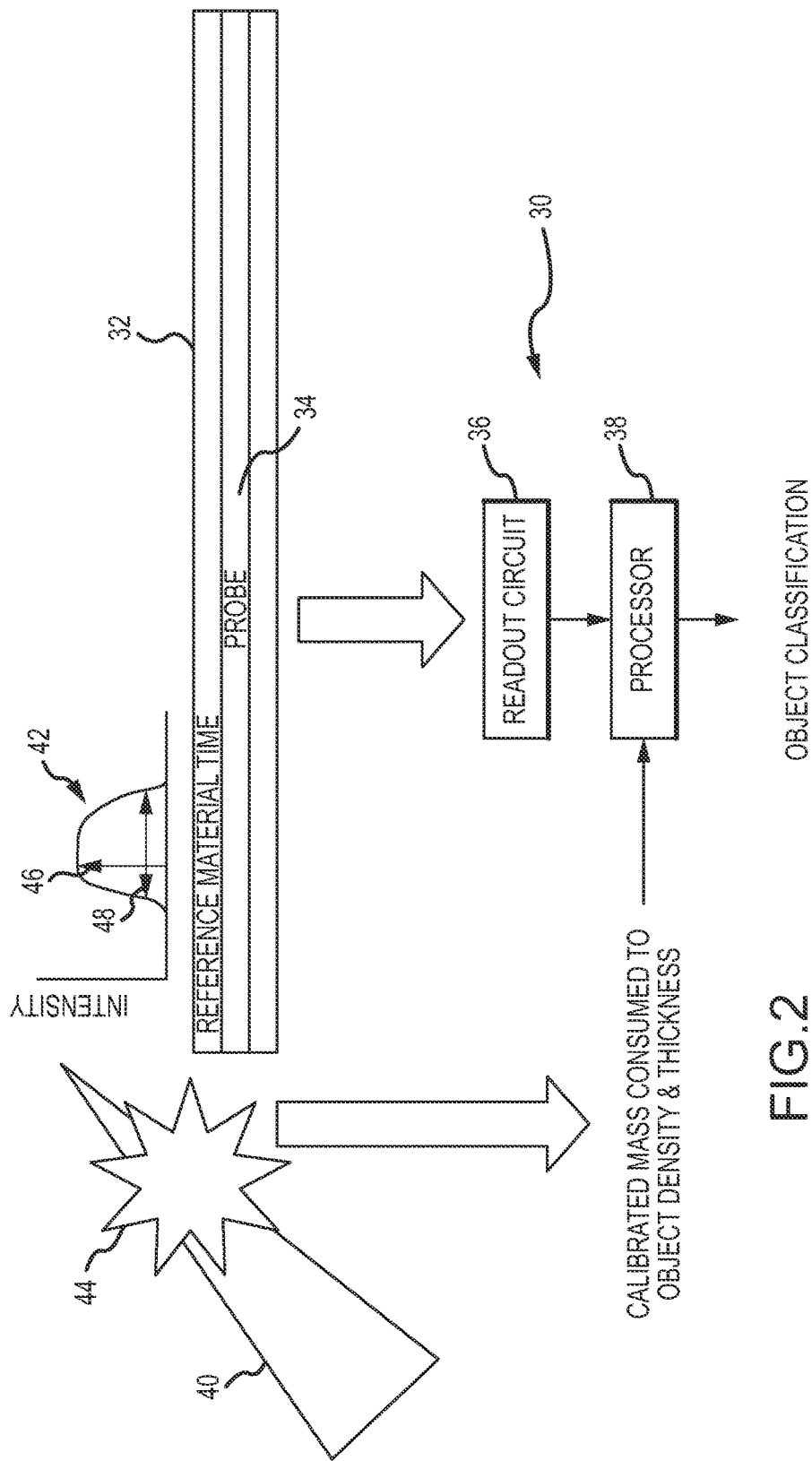
FIG. 2 is a block diagram of an embodiment of the impact sensor.

As described above, shock and impact sensors that detect sudden movements, changes, or severe impacts at a predetermined level and indicate whether that level has been exceeded exist in a variety of configurations. U.S. Patent Pub 2010/0307353 described an optical fiber impact sensor configured to detect and transmit thresholded impact data before the monitor is destroyed.

The present invention seeks to extract additional information about the impact, and more particularly information regarding the density and possibly thickness of the impacted object. Such information may be used, for example, to classify the object.

In ultra-high or hyper-velocity impacts, impacts greater than 1,000 m/s up to approximately 15,000 m/s the mass of the objects is consumed, it changes state from a solid material into a pulse of energy in the form of a flash of light and heat. Information characterizing the velocity of impact and the density and thickness of the impact objects is encoded into that pulse of energy. The pulse height provides information about impact velocity and the density of the impacted object. The pulse width provides information about impact velocity and the thickness of the impacted object. The present invention described an impact sensor that is configured to measure and extract this information.

Referring now to FIGS. 1a and 1b, a projectile is outfitted with an impact sensor that measures and transmits properties of the pulse of energy generated upon impact. The projectile itself may be configured to explode, destroy with kinetic energy, embed in or pass through an object with a relative closing velocity greater than 1,000 m/s up to about 15,000 m/s. As shown in FIG. 1a, a projectile 10 includes a probe 12 that extends forward of the projectile and is in communication with electronics 14 aft of the projectile. The electronics read out outputs from probe 12 as the probe (and impacted object) are consumed at impact and transmits information to a remote location before the electronics are consumed. As shown in FIG. 1b, a kill vehicle (KV) 20 includes a probe 22 that is mounted on the KV's sunshade 24. The probe is coupled to electronics aft of the KV to readout and transmit information to a remote location.

Referring now to FIG. 2, an embodiment of an impact sensor 30 comprises a reference material 32, a probe 34 along the length of the reference material, a readout circuit 36 configured to readout a probe output and a processor 38 configured to process the probe output to classify the impacted object as one of the known objects. Processor 38 may be positioned with the readout circuit or remotely to receive transmission of the probe outputs.

At ultra-high or hyper velocities, impact of sensor 30 with an object 40 consumes both the reference material 32 and object material at the point of impact. This consumption of material, changing its state from a solid to energy, produces a pulse of energy 42 in the form of a flash 44 and heat. The pulse height 46 provides information about impact velocity and the density of the impacted object. The pulse width 48 provides information about impact velocity and the thickness of the impacted object.

Reference material 32 and probe 34 are configured such that varying and known amounts of the material are consumed during impact with different objects of known density at closing velocities within a specified range to generate probe outputs indicative of the amount and rate of material consumed. Readout circuit 36, which can be analog or digital, reads out a temporal sequence of one or more probe outputs that encode the velocity, density and thickness parameters. Processor 38 processes the outputs to extract (implicitly or explicitly) the parameters to characterize and/ or classify the object. The processor may explicitly calculate values for the density and/or thickness, for example. Alternately, the processor could implement a set of matched filters, each designed based on the density and thickness properties of a known object, thereby implicitly calculating the parameters. The process can use the estimate of actual impact velocity to compensate for any variances to an expected impact velocity.

Reference material 32 may be an independent element of just the impact sensor or may be integrated with the projectile. The reference material must be selected and configured to match the "dynamic range" of expected impacts with different objects within a specified range of relative impact velocities. The density and thickness (total mass) of objects may vary widely or little. For example, in a ballistic missile defense system a KV may target and impact a balloon countermeasure, debris or the hardened nuclear warhead. Each of these objects having a very different mass signature. In other embodiments, the target package may comprise only hardened objects whose density and thickness are similar.

Accordingly, reference material 32 should have an appropriate density and total mass such that in the expected velocity range, the thinnest/lightest object consumes sufficient material to produce a measurable output and the thickest/densest objects consume different amounts of material to produce differentiated outputs. The amount of mass consumed, and the rate of consumption, are calibrated to object density and thickness and stored in the processor. Possible reference materials may include, but are not limited to, various composites, various ceramics or glasses, various metals such as steel, titanium, depleted uranium, etc.

Probe 34 extends along the length of the reference material from a forward impact area to a rear area where it is coupled to the readout circuit. Probe 34 generates probe outputs as the mass of reference material is consumed. The probe must generate and convey these probe outputs very quickly to the readout circuit to stay in front of the shock wave produced by the pulse of energy before it consumes the readout circuit.

As will be described below, we have identified three different types of probes, each of which can be implemented with a variety of technologies, e.g., electronic, optical, acoustic or RF. A first type of probe provides a path to convey the optical or electrical pulse created on impact to the readout circuit. A second type of probe includes multiple electronic or optical probe elements at different depths of the reference material. As the reference material is consumed, a number of probe elements are broken interrupting the signal and causing the probe element output to change state. A third type of probe uses a source of energy (RF, optical, acoustical) to inject energy into a cavity to create a standing wave pattern. As the cavity is consumed, the standing wave pattern collapses and releases the stored energy in the form of a pulse.

Figure 3:
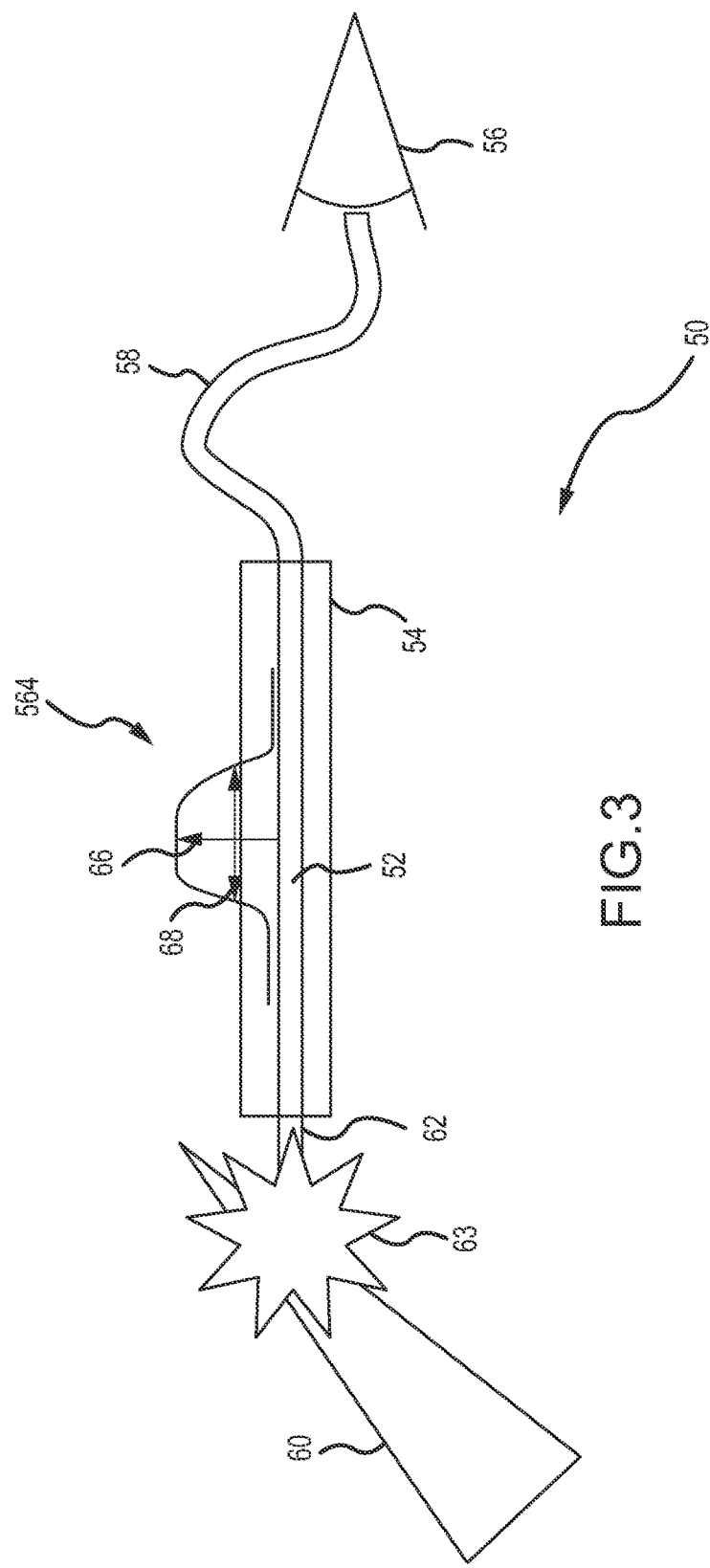
FIG. 3 is a diagram of an embodiment of a fiber optic impact sensor.

Referring now to FIG. 3, an embodiment of an impact sensor 50 comprises a fiber optic probe 52 embedded in a reference material 54. Reference material 54 may be a material such as various composites, various ceramics or glasses, various metals such as steel, titanium, depleted uranium, etc or it may be the fiber optic material itself. Fiber optic probe 52 is coupled to an optical readout 56 aft by a connecting fiber 58. In this configuration, the optical readout 56 transmits the raw data to remote location for processing. At impact with an object 60, at least some of the reference material 54 and fiber optic probe 52 towards the tip 62 of the probe will be consumed. The denser or thicker the impacted object the more of the material and probe that will be consumed.

The plasma 63 formed and heat generated in the impact will generate an optical pulse 64 both inside and outside the fiber optic probe 52. The pulse inside the fiber will travel down the probe at approximately two-thirds the speed of light to optical readout 54 where its pulse height 66 and pulse width 68 can be readout. The readout circuit may extract the height and width parameters directly or may sample the pulse at a sufficiently high rate to capture the height and width information. Pulse height is proportional to the kinetic energy of the impact, which provides velocity and density information. Pulse width is proportional to the time the probe travels through the impacted object, which provides velocity and thickness information. Knowing the properties of the reference material and probe, the data can be processed to extract density and thickness information of the impacted object.

Figure 4:
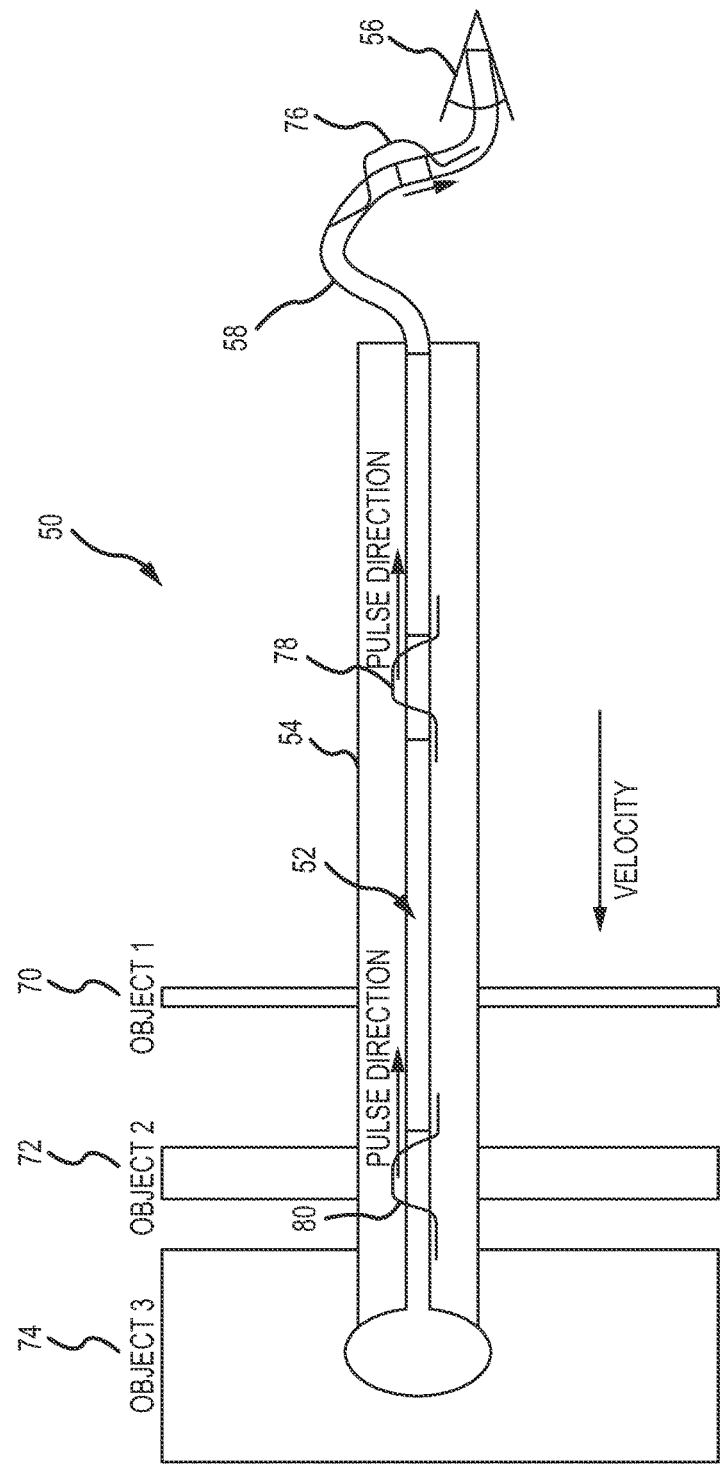
FIG. 4 is a diagram illustrating use of the fiber optic impact sensor to detect and characterize impacts with multiple objects.

Referring now to FIG. 4, as illustrated impact sensor 50 has impacted and passed through relatively light, thin objects 1 70 and 2 72 and has impacted a denser, thicker object 3 74. At each impact, a portion of the reference material 54 and fiber optic probe 52 are consumed generating three separate optical pulse 76, 78 and 80 that travel down the fiber optic probe 52 through connecting fiber 58 to readout circuit 56 that reads out and transmits information about each successive pulse thereby providing information, possibly classification, of each successive object.

Figure 5:
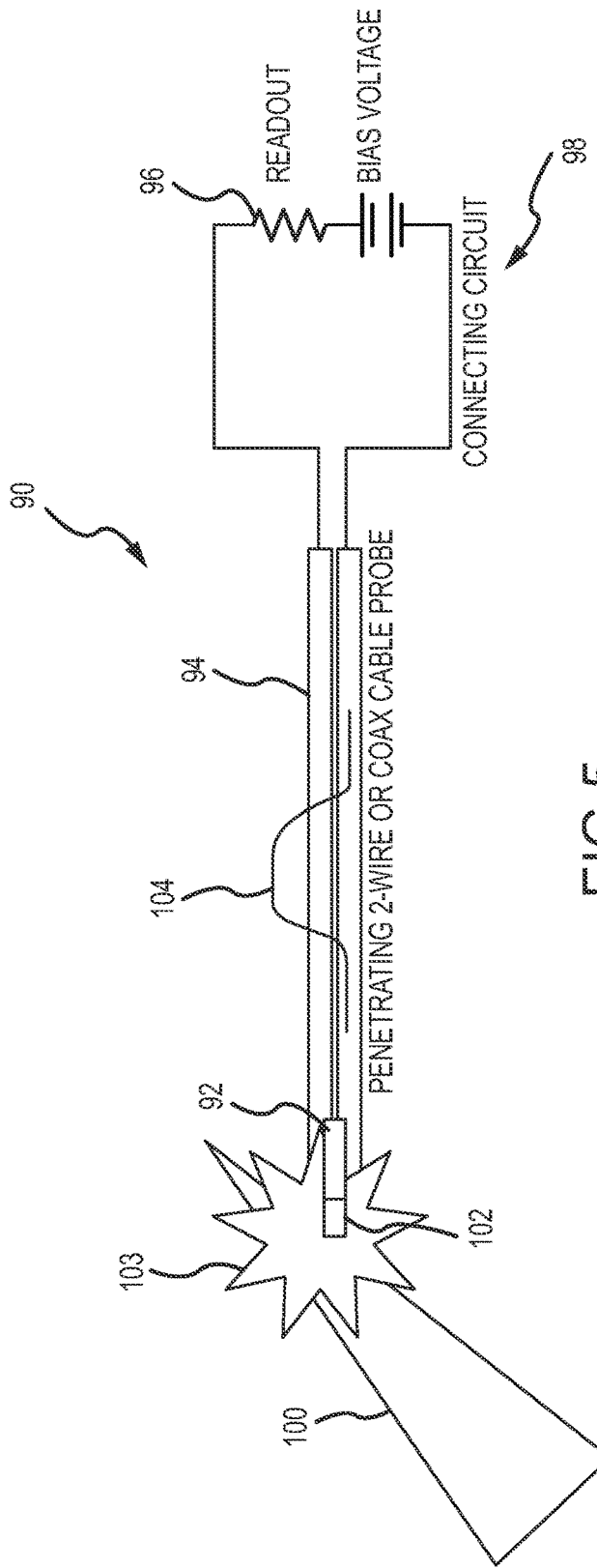
FIG. 5 is a diagram of an embodiment of a two-conductor electrical impact sensor.

Referring now to FIG. 5, an embodiment of an impact sensor 90 comprises a two-conductor (two-wire or coaxial cable) probe 92 embedded in a reference material 94. Two-conductor probe 92 is coupled to an electronic readout 96 aft by a connecting circuit 98. In this configuration, the electronic readout 96 transmits the raw data to remote location for processing. At impact with an object 100, at least some of the reference material 94 and two-conductor probe 92 towards the tip 102 of the probe will be consumed. The denser or thicker the impacted object the more of the material and probe that will be consumed.

The plasma 103 formed and heat generated in the impact is conductive so the two-conductors, parallel or coaxial, can be used as a probe. The two conductors are biased so that one conductor acts as a cathode (attracting positive ions) and the other acts as an anode (attracting negative electrons). A signal pulse 104 travels down the two-conductor probe 92 at approximately two-thirds the speed of light, just as with the fiber optic probe, to electronic readout 94 where its pulse height and pulse width can be readout.

Referring now to FIGS. 6a and 6b, an embodiment of an impact sensor 110 comprises a multi-element probe 120. Multi-element probe 120 comprises multiple probe elements 122, electronic or fiber-optic, embedded at different depths in a reference material 124. A source 126 such as a voltage source or an optical source is coupled to one end of each of the probe elements 122. A readout circuit 128 is coupled to the other end of each of the probe elements 122. Readout circuit 128 reads out a certain state 130 e.g., a "1" under normal conditions. If a probe element is broken, its output state changes e.g., from a "1" to a "0". Readout circuit 128 polls the output state of the elements at a very high rate sufficient to detect the temporal changes in the output states of the different probe elements 122 as the reference material and probe elements at the different depths are broken. The density and thickness characteristics of the impact object that are encoded in the pulse of energy are encoded into the number and rate of breakage of the probe elements 122.

Referring now to FIGS. 7a and 7b, an embodiment of an impact sensor 130 comprises a probe 132 and a reference material 134. A source 136, RF, optical or acoustical, injects energy into probe 132 to create a standing wave pattern 138. As the reference material and probe are consumed, the standing wave pattern collapses and the energy stored in the standing wave travels out of opposite end of the probe forming a pulse 140 that is coupled to a readout circuit 142 (optical detector, RF receiver or acoustic receiver). There will always be some amount of energy 144 exiting the probe, but during impact the signal 146 will be much stronger. The probe may be configured as a resonant cavity, Fabry Perot or a microwave cavity, to produce an even stronger pulse.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

We claim:

1. An impact sensor, comprising:
   a reference material configured such that varying and known amounts of the material are consumed during impact with different objects of known density at closing velocities within a specified range, wherein consumption of the reference material at impact produces a pulse of energy;
   a probe along the length of the reference material, said probe configured to provide a path to conduct the pulse of energy and generate one or more probe outputs indicative of the amount and rate of material consumed during impact;
   a circuit configured to readout the one or more probe outputs; and
   a processor configured to process the one or more probe outputs and extract height and width of the pulse of energy, estimate the density of and classify the impacted object as one of the known objects.

2. The impact sensor of claim 1, wherein the reference material and probe extend from an impact point in a forward section of a projectile aft to a rear section where the probe is coupled to the circuit such that the circuit may receive and readout the probe output before the circuit is consumed.

3. The impact sensor of claim 1, wherein the projectile is configured to explode, destroy with kinetic energy, embed or pass through the object.

4. The impact sensor of claim 1, wherein the closing velocity at impact is at least 1,000 m/s.

5. The impact sensor of claim 1, wherein the probe comprises an optical fiber that provides an optical path as the path, to conduct the pulse to the readout circuit, which comprises an optical detector.

6. The impact sensor of claim 1, wherein the probe comprises a two-wire or coaxial cable that provides an electrical path as the path, to conduct the pulse to the readout circuit, which comprises an electronic readout circuit.

7. The impact sensor of claim 1, wherein the probe comprises multiple probe elements at different depths of the reference material and a source that provides a signal to each of the probe elements, wherein consumption of the reference material breaks a number of probe elements interrupting the signal and causing the probe output to change state, wherein the circuit is configured to readout the states of the multiple probe elements.

8. The impact sensor of claim 7, wherein the probe elements are optical or electronic.

9. The impact sensor of claim 1, wherein the probe comprises a source that is configured to inject energy into a cavity to create a standing wave pattern, wherein consumption of the reference material at impact produces a pulse of energy that consumes the cavity causing the standing wave pattern to collapse and release stored energy in the form of a pulse, wherein the circuit reads out probe outputs that characterize the pulse.

10. The impact sensor of claim 9, wherein the source is a source of RF, optical or acoustic energy.

11. An impact sensor, comprising:
    a reference material configured such that varying amounts of the material are consumed during impact with objects of differing density and thickness at closing velocities within a specified range to form a plasma that produces a pulse of energy wherein consumption of the reference material at impact produces a pulse of energy;
    a probe along the length of the reference material, said probe configured to provide a path to conduct the pulse of energy and generate outputs indicative of the amount of material consumed during impact;
    a circuit configured to readout a time sequence of outputs; and
    a processor configured to receive and process the time sequence of outputs and extract height and width of the pulse of energy and estimate the density and thickness of the impacted object.

12. The impact sensor of claim 11, wherein the probe provides an optical or electronic path as the path, to conduct the pulse of energy to the readout circuit that reads out height and width of the pulse in one or more probe outputs.

13. The impact sensor of claim 11, wherein the probe comprises multiple electronic or optical probe elements at different depths of the reference material and a source that provides an electrical or optical signal to each of the probe elements, wherein the pulse of energy breaks a number of probe elements interrupting the signal and causing the probe output to change state, wherein the circuit is configured to readout the states of the multiple probe elements.

14. The impact sensor of claim 11, wherein the probe comprises a source that is configured to inject energy into a cavity to create a standing wave pattern, wherein consumption the pulse of energy consumes the cavity causing the standing wave pattern to collapse and release stored energy in the form of a pulse, wherein the circuit reads out probe outputs that characterize the pulse.

15. An impact sensor, comprising:
- a projectile configured to explode, destroy with kinetic energy, embed or pass through an object with a closing velocity greater than 1,000 m/s;
- a reference material and probe that extend from an impact point in a forward section of the projectile aft to a rear section, said reference material configured such that varying amounts of the material are consumed during impact with different objects to produce a pulse of energy, said probe configured to provide a path to conduct the pulse of energy and generate one or more probe outputs indicative of the amount of material consumed during impact;
- a circuit in the rear section of the projectile, said circuit configured to readout and transmit a time sequence of probe outputs; and
- a remote processor configured to receive and process the time sequence of probe outputs and extract height and width of the pulse of energy and estimate the density of or classify the impacted object.

16. The impact sensor of claim 15, wherein the probe provides an optical or electronic path as the path, to conduct a pulse of energy to the readout circuit that reads out height and width of the pulse in one or more probe outputs.

17. The impact sensor of claim 15, wherein the probe comprises multiple electronic or optical probe elements at different depths of the reference material and a source that provides an electrical or optical signal to each of the probe elements, wherein the consumption of the material breaks a number of probe elements interrupting the signal and causing the probe output to change state, wherein the circuit is configured to readout the states of the multiple probe elements.

18. The impact sensor of claim 15, wherein the probe comprises a source that is configured to inject energy into a cavity to create a standing wave pattern, wherein consumption of the reference material destroys the cavity causing the standing wave pattern to collapse and release stored energy in the form of a pulse, wherein the circuit reads out probe outputs that characterize the pulse.

* * * * *